United States Patent
Ansley et al.

(10) Patent No.: US 9,358,562 B2
(45) Date of Patent: Jun. 7, 2016

(54) AIR SUPPLY DEVICE AND RELATED METHODS OF MANUFACTURE

(71) Applicant: Prolitec Inc., Seattle, WA (US)

(72) Inventors: Matthew Ansley, Muskego, WI (US); Nathan Sward, Milwaukee, WI (US); Howard Tanner, Wauwatosa, WI (US)

(73) Assignee: Prolitec Inc., Milwaukee, WI (US)

( * ) Notice: Subject to any disclaimer, the term of this patent is extended or adjusted under 35 U.S.C. 154(b) by 0 days.

(21) Appl. No.: 14/693,716

(22) Filed: Apr. 22, 2015

(65) Prior Publication Data

US 2015/0300345 A1 Oct. 22, 2015

Related U.S. Application Data

(60) Provisional application No. 61/982,504, filed on Apr. 22, 2014.

(51) Int. Cl.
*F04B 39/12* (2006.01)
*B05B 7/24* (2006.01)
(Continued)

(52) U.S. Cl.
CPC ............... *B05B 7/2489* (2013.01); *A61L 9/14* (2013.01); *A61L 9/145* (2013.01); *A61M 11/02* (2013.01); *B01F 3/04007* (2013.01); *B01F 3/04021* (2013.01); *B01F 3/0446* (2013.01); *B05B 1/26* (2013.01); *B05B 7/24* (2013.01);
(Continued)

(58) Field of Classification Search
CPC ........ F04B 43/04; F04B 43/043; F04B 23/04; F04B 41/06; F04B 43/02; F04B 43/025; F04B 43/026; F04B 45/022; F04B 45/024; F04B 45/027; F04B 45/041; F04B 45/043; F04B 45/045; F04B 45/047; F04B 39/0044; F04B 39/121; F04B 39/127
USPC .......................................................... 417/363
See application file for complete search history.

(56) References Cited

U.S. PATENT DOCUMENTS 2,240,307 A * 4/1941 List ............................... 417/412
2,928,589 A * 3/1960 Davey ................. F04B 39/0033
181/403

(Continued)

FOREIGN PATENT DOCUMENTS

EP 0 753 664 A1 1/1997
GB 2365081 A 2/2002

OTHER PUBLICATIONS

International Search Report and Written Opinion, mailed Oct. 5, 2015, for International Application No. PCT/US2015/027149, 11 pages.

*Primary Examiner* — Justin Jonaitis
*Assistant Examiner* — Charles Nichols
(74) *Attorney, Agent, or Firm* — Seed IP Law Group PLLC (57) ABSTRACT

A pump device is provided including: a unitary pump frame; an electromagnet arrangement that includes a winding wrapped around a portion of the unitary pump frame; a diaphragm assembly coupled to the unitary pump frame, which includes a movable diaphragm and a manifold; and a pump arm having a proximal end coupled to the unitary pump frame and a distal end supporting a permanent magnet to interact with the electromagnet arrangement to cause the pump arm to swing back and forth during operation to displace the diaphragm and discharge an air stream from the pump device. Related methods of manufacture are also provided.

25 Claims, 9 Drawing Sheets

(51) Int. Cl.
| | | |
|---|---|---|
| *A61L 9/14* | (2006.01) | |
| *B01F 3/04* | (2006.01) | |
| *F24F 3/16* | (2006.01) | |
| *F04B 39/00* | (2006.01) | |
| *F04B 45/047* | (2006.01) | |
| *A61M 11/02* | (2006.01) | |
| *B05B 1/26* | (2006.01) | |

(52) U.S. Cl.
CPC .......... *F04B 39/0044* (2013.01); *F04B 39/121* (2013.01); *F04B 39/127* (2013.01); *F04B 45/047* (2013.01); *F24F 3/16* (2013.01); *A61L 2209/134* (2013.01); *B01F 2215/009* (2013.01); *F24F 2003/1689* (2013.01)

(56) References Cited

U.S. PATENT DOCUMENTS

| | | | |
|---|---|---|---|
| 3,339,094 A * | 8/1967 | Shopsky | 417/313 |
| 3,545,894 A | 12/1970 | Lovitz | |
| 3,825,374 A | 7/1974 | Kondo | |
| 3,830,596 A | 8/1974 | Kondo | |
| 4,162,876 A | 7/1979 | Kolfertz | |
| 4,501,664 A * | 2/1985 | Heil et al. | 210/614 |
| 4,877,378 A * | 10/1989 | Saggers | 417/299 |
| 5,213,484 A * | 5/1993 | Hashimoto et al. | 417/312 |
| 5,236,168 A * | 8/1993 | Roy | 248/546 |
| 5,554,012 A * | 9/1996 | Itakura | 417/410.1 |
| 6,007,307 A * | 12/1999 | Sonoda | 417/312 |
| 6,379,124 B1 * | 4/2002 | Lai | 417/410.1 |
| 6,405,944 B1 | 6/2002 | Benalikhoudja | |
| 6,912,866 B2 * | 7/2005 | Seo | F04B 39/0044 181/207 |
| 7,363,737 B2 | 4/2008 | Benalikhoudja | |
| 7,712,683 B2 | 5/2010 | Robert et al. | |
| 7,930,068 B2 | 4/2011 | Robert et al. | |
| 8,006,698 B2 | 8/2011 | Boehm et al. | |
| 8,596,264 B2 | 12/2013 | Sommer | |
| 8,602,396 B1 | 12/2013 | V et al. | |
| 8,855,827 B2 | 10/2014 | Weening et al. | |
| 2005/0047923 A1 | 3/2005 | Li et al. | |
| 2006/0219814 A1 | 10/2006 | Benalikhoudja | |
| 2006/0237090 A1 | 10/2006 | Benalikhoudja | |
| 2009/0010778 A1 * | 1/2009 | Wang | 417/413.1 |
| 2010/0086418 A1 | 4/2010 | Sevy | |

* cited by examiner

AIR SUPPLY DEVICE AND RELATED METHODS OF MANUFACTURE

BACKGROUND

1. Technical Field

The present disclosure relates to air supply devices and, more particularly, to air supply devices (e.g., air pumps) suitable for supplying air to liquid diffusion devices for air treatment purposes and related methods of manufacture.

2. Description of the Related Art

Air supply devices (e.g., air pumps) are known which include an electromagnet assembly having a core and a coil powered by an AC power source, a vibrating arm having a permanent magnet at its end, which is oscillated within an alternating magnetic field of the electromagnet assembly, a cup or bowl-shaped elastic diaphragm fixed at the intermediate portion of the vibrating arm, and a valve housing having inlet and outlet one-way valves to open or shut inlet and outlet ports. The diaphragm is arranged relative to the valve housing so as to transmit the oscillation of the vibrating arm to supply air to an external device through a suitable conduit. An example of such an air pump is shown and described in U.S. Pat. No. 3,825,374. Conventional air pumps of this type, however, may suffer from a variety of deficiencies or drawbacks, including, for example, being overly complex or cumbersome to manufacture. Conventional air pumps may also be unnecessarily large, noisy, inefficient, and/or unreliable and may transmit undesirable vibrations to surrounding structures.

BRIEF SUMMARY

The air supply devices or pumps described herein are provided in particularly efficient form factors for use in connection with a wide variety of applications, including, for example, the supply of pressurized air to liquid diffusion devices for air treatment purposes. The air supply devices may also be particularly reliable and efficient, may have relatively small or compact form factors, and may exhibit low noise levels and low vibration transmission to surrounding structures.

At least one embodiment of an air supply device in the form of an air pump may be summarized as including: a unitary pump frame; an electromagnet arrangement including a winding wrapped around a portion of the unitary pump frame; a diaphragm assembly coupled to the unitary pump frame, the diaphragm assembly including a movable diaphragm and a manifold; and a pump arm having a proximal end and a distal end, the proximal end of the pump arm coupled to the unitary pump frame and the distal end of the pump arm including a magnet to interact with the electromagnet arrangement to cause the pump arm to swing back and forth to displace the movable diaphragm during operation of the air pump. The portion of the unitary pump frame around which the winding of the electromagnet arrangement is wrapped may resemble a bobbin having a hollow core and opposing flanges.

The air pump may further include a plurality of flexible, resilient tethers extending from the unitary pump frame for suspending the air pump within an internal cavity of a housing or other host device. The plurality of flexible, resilient tethers and unitary pump frame may be formed via a multi-material injection molding process to form an integrated frame structure with tethers extending therefrom. Additionally, a manifold seal may be formed via the multi-material injection molding process to form an integrated structure. The plurality of flexible, resilient tethers may include barbs to selectively engage apertures of the housing or the host device to maintain the unitary pump frame suspended within the internal cavity. The unitary pump frame may include a pump arm receiving aperture that is sized and shaped to receive a corresponding portion of the proximal end on the pump arm in a press-fit or friction-fit. The unitary pump frame may define a closed perimeter around the diaphragm assembly and the pump arm. The unitary pump frame may include retaining structures positioned to engage each of opposing ends of the manifold of the diaphragm assembly to assist in coupling the manifold to the unitary pump frame.

The electromagnet arrangement may include an electromagnet core having a pair of legs, and the unitary pump frame may include a bulkhead portion having a corresponding pair of apertures to receive the legs of the electromagnet core. The corresponding pair of apertures in the bulkhead portion of the unitary pump frame may be sized and shaped to receive the legs of the electromagnet core in a press-fit or friction-fit. The unitary pump frame may include an upper bulkhead and terminals may be provided at or proximate the upper bulkhead for supplying power to the electromagnet arrangement from an AC power source. The unitary pump frame may be an open-sided structure that is configured to receive the diaphragm assembly and the pump arm as a pump cartridge in a direction transverse to a plane defined by an oscillating motion of the pump arm.

The air pump may be part of an air treatment system including a housing and a diffusion head received in the housing and may be operably connected to the diffusion head for diffusing liquid contained in the housing. The air treatment system may further include a plurality of flexible, resilient tethers extending from the unitary pump frame to suspend the air pump within an internal cavity of the housing. A sound deadening or muffling device may be provided in the housing to reduce noise emanating therefrom.

At least one embodiment of a manufacturing method may be summarized as including: providing a unitary pump frame with a winding of an electromagnet arrangement wrapped around a portion thereof; coupling a pump cartridge to the unitary pump frame, the pump cartridge including a manifold subassembly and a pump arm subassembly; and thereafter coupling an electromagnet core of the electromagnet arrangement to the unitary pump frame such that at least a portion of the electromagnet core passes through the winding of the electromagnet arrangement.

The method may further include prior to coupling the pump cartridge to the unitary pump frame, press-fitting or friction-fitting the manifold subassembly into a movable diaphragm of the pump arm subassembly. Coupling the pump cartridge to the unitary pump frame may include press-fitting or friction-fitting a proximal end of a pump arm of the pump arm subassembly into a corresponding aperture of the unitary pump frame. Coupling the pump cartridge to the unitary pump frame may further include securing the manifold subassembly to the unitary pump frame with a fastener. Coupling the electromagnet core of the electromagnet arrangement to the unitary pump frame may include press-fitting or friction-fitting leg portions of the electromagnet core into corresponding apertures of the unitary pump frame.

The method may further include suspending the unitary pump frame within an internal housing cavity via a plurality of flexible, resilient tethers and selectively adjusting a tension of one or more of the plurality of flexible, resilient tethers. The method may further include providing a sound deadening or muffling device in the internal housing to reduce noise emanating therefrom. The method may also include coupling an air outlet of the manifold subassembly to a liquid diffusion device for air treatment purposes.

DETAILED DESCRIPTION

In the following description, certain specific details are set forth in order to provide a thorough understanding of various disclosed embodiments. However, one skilled in the relevant art will recognize that embodiments may be practiced without one or more of these specific details. In other instances, well-known devices, structures and techniques associated with air supply devices (e.g., air pumps), components thereof and related methods of manufacture may not be shown or described in detail to avoid unnecessarily obscuring descriptions of the embodiments.

Unless the context requires otherwise, throughout the specification and claims which follow, the word "comprise" and variations thereof, such as, "comprises" and "comprising" are to be construed in an open, inclusive sense, that is as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The present disclosure relates generally to air supply devices and more particularly to air supply devices suitable for supplying air for a variety of different purposes and related methods of manufacture. For example, the air supply devices 10 described herein may be included or otherwise coupled to a liquid diffusion device for supplying air to the liquid diffusion device for air treatment purposes. Such liquid diffusion devices may include, for example, those shown and described in Applicant's co-pending application Ser. Nos. 14/612,066 and 14/612,072, both filed on Feb. 2, 2015, which are incorporated herein by reference in their entireties.

Figure 1:
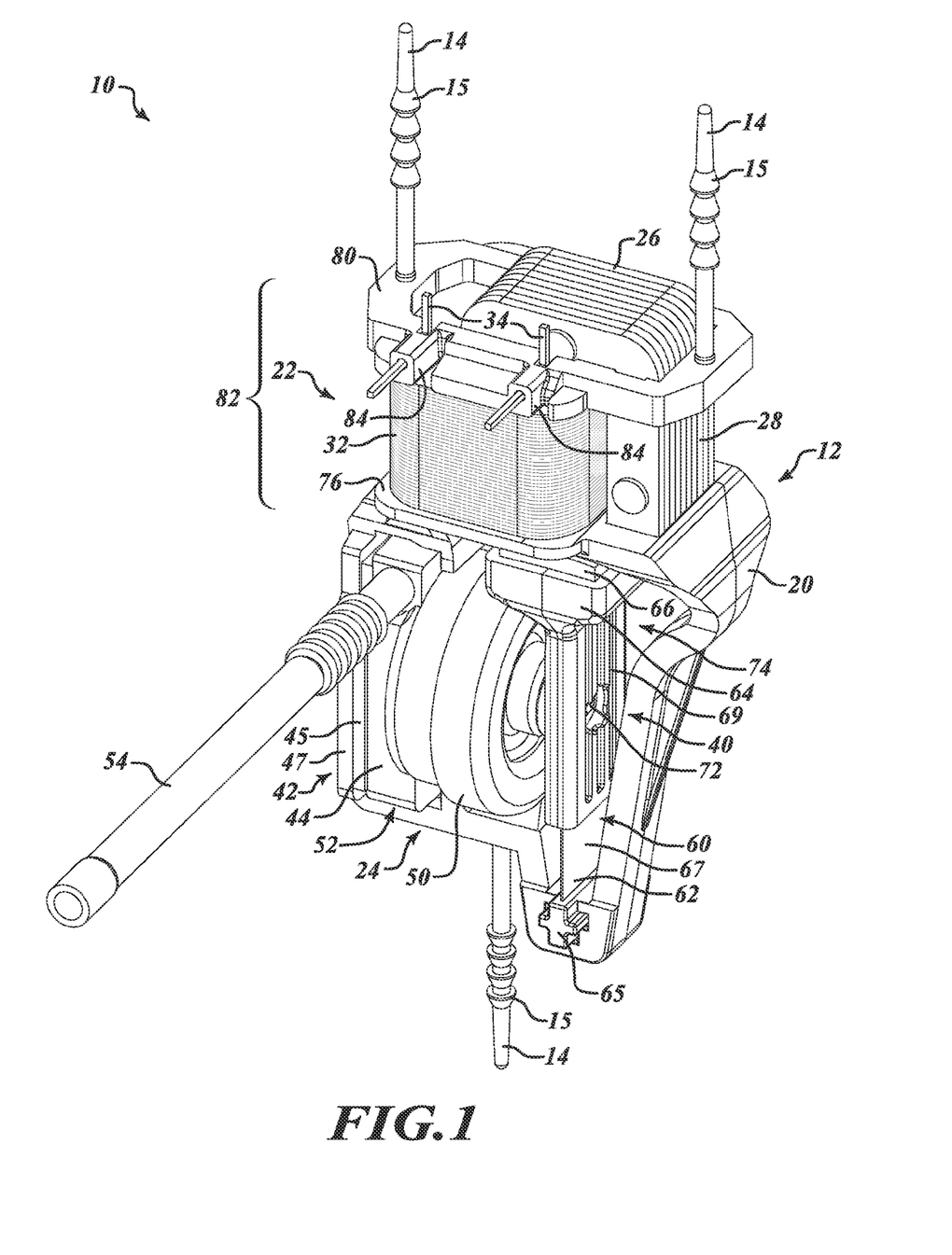
FIG. 1 is an isometric view of an air supply device, according to one embodiment.
Figure 2:
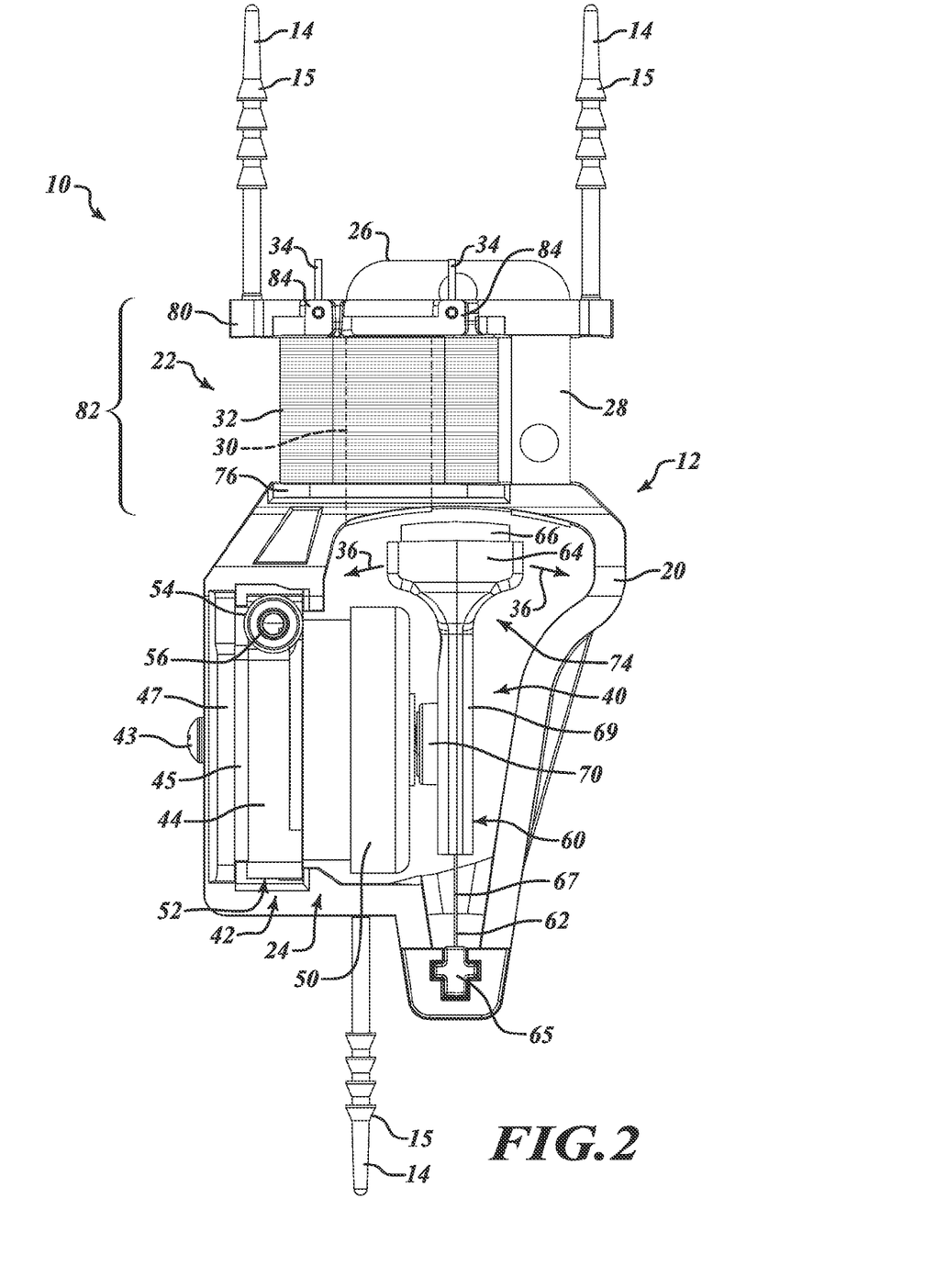
FIG. 2 is a front elevational view of the air supply device of FIG. 1.

With reference to FIGS. 1 and 2, one example embodiment of an air supply device 10 in the form of an air pump is provided. The air supply device 10 includes a frame structure 12 coupleable to a housing 102 (FIG. 10) or other host device via a plurality of flexible, resilient tethers 14 that extend from the frame structure 12 for suspending the air supply device 10 within an internal cavity 110 of the housing 102 or other host device. The frame structure 12 may include a unitary frame body 20 that provides a generally rigid foundation for other components of air supply device 10. For example, the unitary frame body 20 provides a foundation for an electromagnet arrangement 22 and a pump cartridge 24 that is provided adjacent the electromagnet arrangement 22 to interact with the same during operation of the air supply device 10. The electromagnet arrangement 22 may include an electromagnet core 26 with opposing leg portions 28, 30 that define opposing poles and a winding 32 (e.g., 1,250 turns of 32 gauge wire) surrounding one of the leg portions 30 and a bobbin or bobbin-like structure 82 of the unitary frame body 20. The electromagnet core 26 may comprise a laminated stack of plates pinned or otherwise secured together. The electromagnet arrangement 22 may further include electrical terminals 34 coupled to the winding 32 for supplying AC power to the electromagnet arrangement 22 during operation to create an alternating magnet field. The electrical terminals 34 may be folded down in front of the winding 32 to reduce the size of the air supply device 10.

With continued reference to FIGS. 1 and 2, the pump cartridge 24 may include a pump arm subassembly 40 coupled to a manifold subassembly 42. The manifold subassembly 42 may include a manifold 44 with internal valving 46, 48 (FIGS. 8 and 9) arranged to operate in conjunction with a movable diaphragm 50 of the pump arm subassembly 40 to draw air into the manifold 44 via an air inlet 52 provided at one end of the manifold 44 and to discharge air out via an outlet conduit 54 coupled to an air outlet 56 of an outlet nipple 57 provided at the other end of the manifold 44. More particularly, the pump arm subassembly 40 may include a pump arm 60 having a proximal end 62 and a distal end 64 with the proximal end 62 of the pump arm 60 being coupled to the unitary frame body 20 and with the distal end 64 of the pump arm 60 including a permanent magnet 66 to interact with the electromagnet arrangement 22 to cause the pump arm 60 to swing back and forth during operation of the air supply device 10, as indicated by arrows labeled 36 in FIG. 2, to displace the movable diaphragm 50 and force air to move through the manifold 44 from the inlet 52 to the outlet 56.

Figure 3:
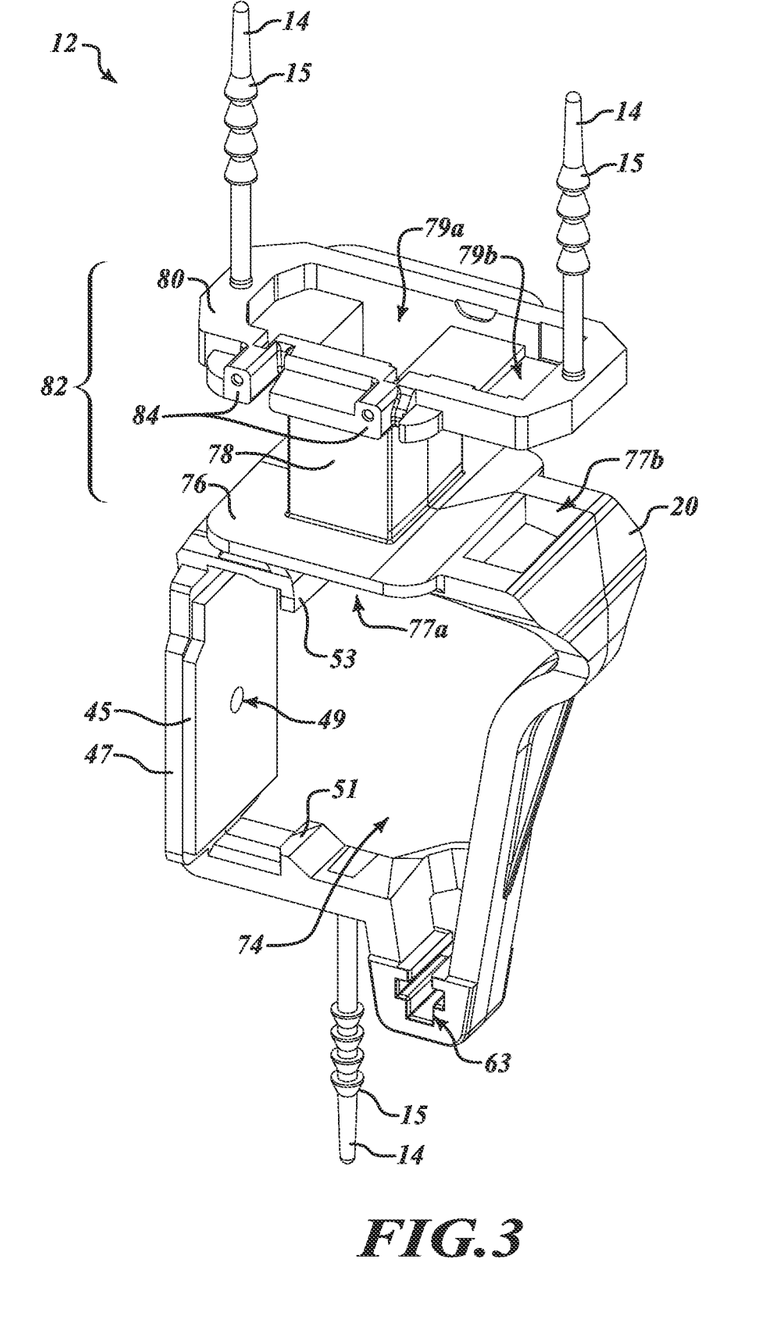
FIG. 3 is an isometric view of a frame structure of the air supply device of FIG. 1.

Additional details of the frame structure 12 of the air supply device 10 are described with reference to FIG. 3. As shown, the frame structure 12 may include the unitary frame body 20 and the plurality of flexible, resilient tethers 14 for suspending the air supply device 10 within the internal cavity 110 of the housing 102 or other host device. In some instances, the plurality of flexible, resilient tethers 14 and unitary frame body 20 may be formed via a multi-material injection molding process to form an integrated frame structure 12 with tethers 14 extending therefrom, as shown in FIG. 3. The frame structure 12 may also include a manifold seal 45 that is formed via a multi-material injection molding process with the unitary frame body 20 and the tethers 14 to form an integrated frame structure 12 having tethers 14 and the manifold seal 45. In this manner, the frame structure 12 shown in FIG. 3 can be supplied for assembly as a single unitary part having different portions with different material properties and related functionality. For example, the unitary frame body 20 may be formed of a rigid or semi-rigid material for providing a foundation or support structure for other components of the air supply device 10, the tethers 14 may be formed of a flexible, resilient material that is configured to suspend the air supply device 10 and isolate and/or dampen motion of the air supply device 10 relative to the housing 102 (FIG. 10) or other host device or structure, and the manifold seal 45 may be formed of compressible seal materials for forming an air-tight seal between the manifold 44 and a manifold backing portion 47 of the frame body 20.

The tethers 14 may be formed to include barbs 15 or other structures for assisting in fastening the air supply device 10 to the housing 102 or other host device. Advantageously, the tethers 14 of the illustrated embodiment may be conveniently fed through corresponding apertures 108 in the housing 102 or other host device and selectively brought into a generally taut or stretched configuration by pulling the tethers 14 until an appropriate one of the barbs 15 passes through the corresponding aperture 108 in a compressed form and then expands to engage the structure of the housing 102 or other host device that surrounds the aperture 108.

The manifold seal 45 may be formed to be generally planar and may have an overall profile that substantially corresponds to that of the manifold 44, which is held in contact with the manifold seal 45 upon assembly. Each of the manifold seal 45 and the manifold backing portion 47 of the frame body may also be provided with an aperture 49 for receiving a fastener 43 therethrough for retaining the manifold 44 of the manifold subassembly 42 in engagement with the manifold seal 45. For this purpose, the manifold 44 may include a boss 55 with an aperture 58 provided therein for receiving the fastener 43, as shown best in FIG. 4. With reference again to FIG. 3, the unitary frame body 20 may further include retaining structures 51, 53 which are positioned to engage each of opposing ends of the manifold 44 of the manifold subassembly 42 to assist in coupling the manifold 44 to the unitary frame body 20 and maintaining a seal at the interface between the manifold 44 and the manifold seal 45.

With reference to FIGS. 1 through 3, other features of the unitary frame body 20 include a pump arm receiving aperture 63 provided at a lower end of the frame body 20 which may be sized and shaped to receive the proximal end 62 on the pump arm 60 with a press-fit or friction-fit. In this manner, the proximal end 62 of the pump arm 60 of the pump arm subassembly 40 may be inserted into the pump arm receiving aperture 63 and secured to the frame body 20 without mechanical fasteners. In some instances, including the illustrated embodiment shown in FIG. 3, the pump arm receiving aperture 63 may extend partially or completely through the frame body 20 in a direction generally perpendicular to a plane defined by the direction in which the pump arm 60 oscillates during operation. The pump arm receiving aperture 63 and the proximal end 62 of the pump arm 60 may have complementary shapes. In some instances, the pump arm receiving aperture 63 and the proximal end 62 of the pump arm 60 may be T-shaped, plus-shaped, or otherwise include projections and corresponding grooves to securely anchor the pump arm 60 in the frame body 20 to prevent rotation of the proximal end 62 of the pump arm 60 as the remaining portion of the pump arm 60 oscillates during operation. For this purpose, the proximal end 62 of the pump arm 60 may include an anchoring device 65 formed around a lower end of a thin flexible arm member 67 of the pump arm 60, such as, for example, by injection molding techniques. The thin flexible arm member 67 may be, for example, spring steel or other similar material, and may be configured to elastically deform during operation while the anchoring device 65 remains effectively static. The thin flexible arm member 67 may be configured to flex in excess of ten million cycles without appreciable deterioration. The pump arm 60 may further include a pump arm body 69 formed around a mid-section and upper end of the thin flexible arm member 67, such as, for example, by injection molding techniques. The permanent magnet 66 may be secured to or otherwise retained in the upper end of the pump arm body 69 opposite the anchoring device 65. A diaphragm coupling structure 70 may be provided in the pump arm body 69 at a mid-section region of the thin flexible arm member 67 for coupling to the movable diaphragm 50. For example, the diaphragm coupling structure 70 may include a boss extending from a side of the pump arm body 69 that includes an aperture for receiving a fastener 72 for interfacing with the movable diaphragm 50 and fixing the movable diaphragm 50 to the pump arm 60 to move in unison therewith during operation.

With continued reference to FIGS. 1 through 3, other features of the unitary frame body 20 include the provision of a closed perimeter structure that surrounds the pump cartridge 24, including the pump arm subassembly 40 and the manifold subassembly 42. The closed perimeter structure may define a central cavity or aperture 74 that extends completely through the frame body 20 such that opposing sides of the frame structure 12 are open. The central cavity or aperture 74 may have a profile that generally reflects a combination of a side profile of the manifold 44 and a swept side profile of the pump arm 60 and movable diaphragm 50 resulting from oscillation of the pump arm 60 and movable diaphragm 50 during operation.

At least one of the tethers 14 may be provided at a lower end of the unitary frame body 20 to extend away from the frame body 20 in a direction parallel to the plane defined by the direction in which the pump arm 60 oscillates during operation. In addition, at least one of the tethers 14 may be provided at an upper end of the unitary frame body 20 to extend away from the frame body 20 in a direction parallel to the plane defined by the direction in which the pump arm 60 oscillates during operation.

An upper end of the frame body 20 may further include a lower platform or flange structure 76, a hollow stem or core portion 78 and an upper flange or bulkhead 80 that defines a bobbin or bobbin-like structure 82 around which the winding 32 of the electromagnet arrangement 22 may be wound. Advantageously, the bobbin or bobbin-like structure 82 is integrally formed as a portion of the frame body 20 which supports all other functional components of the air supply device 10. Each of the lower platform or flange structure 76 and the upper flange or bulkhead 80 may be provided with respective apertures 77a, 77b, 79a, 79b for insertably receiving the opposing leg portions 28, 30 of the electromagnet core 26 of the electromagnet arrangement 22. The apertures 77a, 77b, 79a, 79b may be correspondingly sized and shaped to receive corresponding portions of the opposing leg portions 28, 30 of the electromagnet core 26 of the electromagnet arrangement 22 in a press-fit or friction fit. Respective ends of the opposing leg portions 28, 30 of the electromagnet core 26 may extend beyond the lower platform or flange structure 76 after the air supply device 10 is fully assembled, as shown best in FIG. 2. Lower surfaces of the opposing leg portions 28, 30 of the electromagnet core 26 may be concave and may be correspondingly shaped to reflect a convex surface of the permanent magnet 66 at the distal end 64 of the pump arm 60. The curvature of the convex surface of the permanent magnet 66 and the concave lower surfaces of the opposing leg portions 28, 30 may be selected to maintain a constant air gap between the lower end of electromagnet core 26 and the permanent magnet 66 at the distal end 64 of the pump arm 60, which may advantageously improve efficiency of the air supply device 10.

The unitary frame body 20 may further include terminal structures 84 at or near the upper flange or bulkhead 80 for receiving and/or supporting the electrical terminals 34 of the winding 32 for electrically coupling the electromagnet arrangement 22 with an external AC power source (e.g., 15V AC power source).

Figure 4:
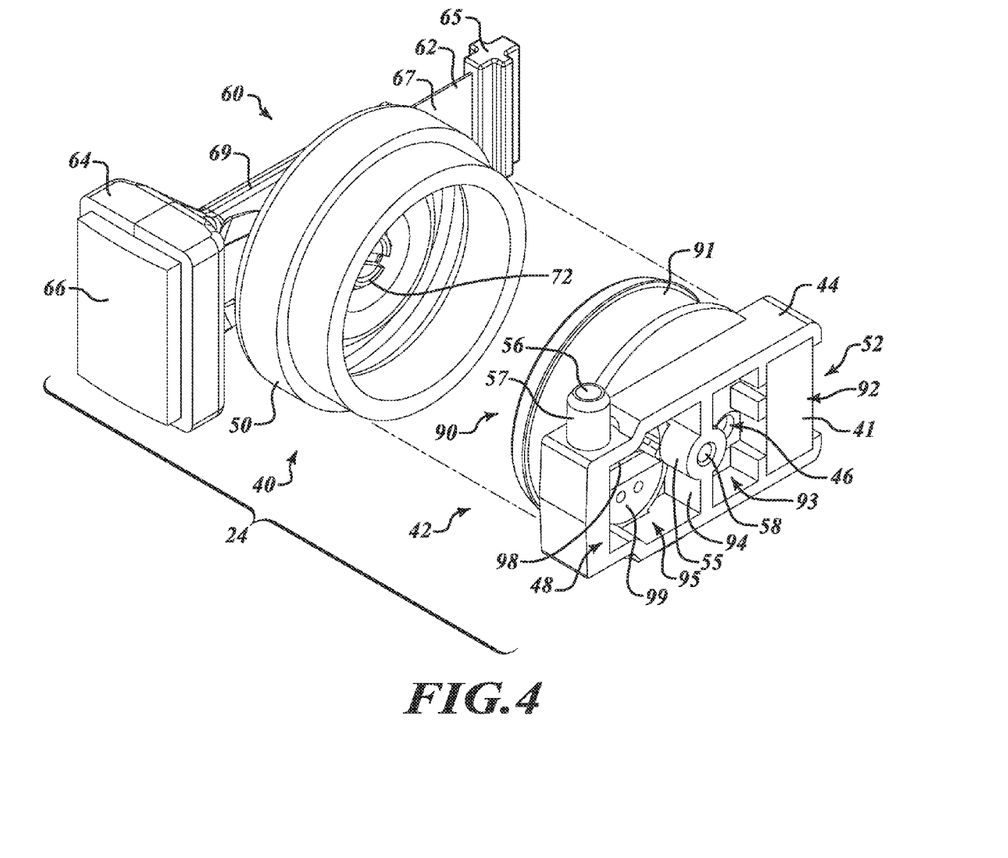
FIGS. 4 through 7 provide a sequence of isometric views illustrating a method of manufacturing the air supply device of FIG. 1, according to one embodiment.

In view of the above, it will appreciated that various methods may be provided for manufacturing the air supply devices 10 described herein. As an example, FIGS. 4 through 7 illustrate one example embodiment of a method of manufacturing the air supply device 10 of FIGS. 1 and 2, with additional features of the manifold subassembly 42 being shown in FIGS. 8 and 9. As depicted in FIG. 4, the method may include coupling the pump arm subassembly 40 to the manifold subassembly 42 to form a pump cartridge 24. Coupling the pump arm subassembly 40 to the manifold subassembly 42 may include inserting (e.g., press-fitting, friction-fitting) a rim 91 of a diaphragm chamber 90 of the manifold subassembly 42 into the movable diaphragm 50 of the pump arm subassembly 40 to create a diaphragm assembly and pump cartridge 24. Prior to coupling the pump arm subassembly 40 to the manifold subassembly 42, the method may include securing the movable diaphragm 50 to the pump arm 60, such as, for example, by fastening the movable diaphragm 50 to the pump arm 60 with a fastener 72 that engages the diaphragm coupling structure 70 of the pump arm body 69.

Figures 8, 9:
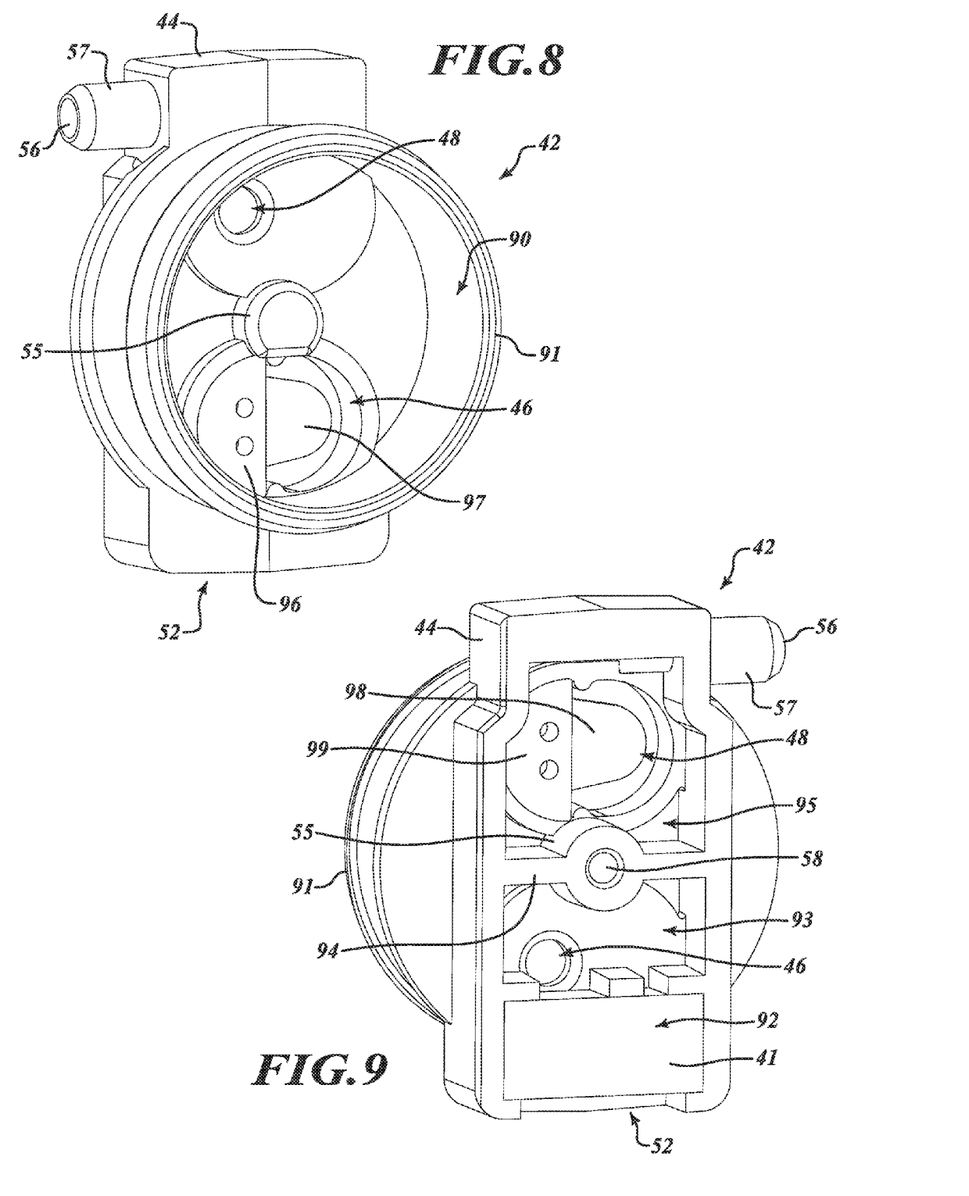
FIGS. 8 and 9 are perspective views of a manifold portion of the air supply device of FIG. 1 from each of opposing sides thereof.

With reference to FIGS. 8 and 9, prior to coupling the pump arm subassembly 40 to the manifold subassembly 42, the manifold 44 may be fitted with an air filter and/or muffler element 41 and internal valves 46, 48 for coordinating the flow of air through the manifold 44 during operation. The air filter and/or muffler element 41 may be insertably received in a corresponding air filter/muffler chamber portion 92 of the manifold 44 to filter air entering inlet 52 before it reaches an inlet chamber 93 that is separated from the diaphragm chamber 90 via a first one-way valve 46, and before reaching an outlet chamber 95 that is separated from the diaphragm chamber 90 via a second one-way valve 48 and also separated from the inlet chamber 93 by a bulkhead 94. Flapper members 96, 98 of the internal valves 46, 48 may be installed and held in place with compressible valve retainer members 97, 99 that are compressed into corresponding spaces formed in the diaphragm chamber 90 and the outlet chamber 95, respectively.

Figure 5:
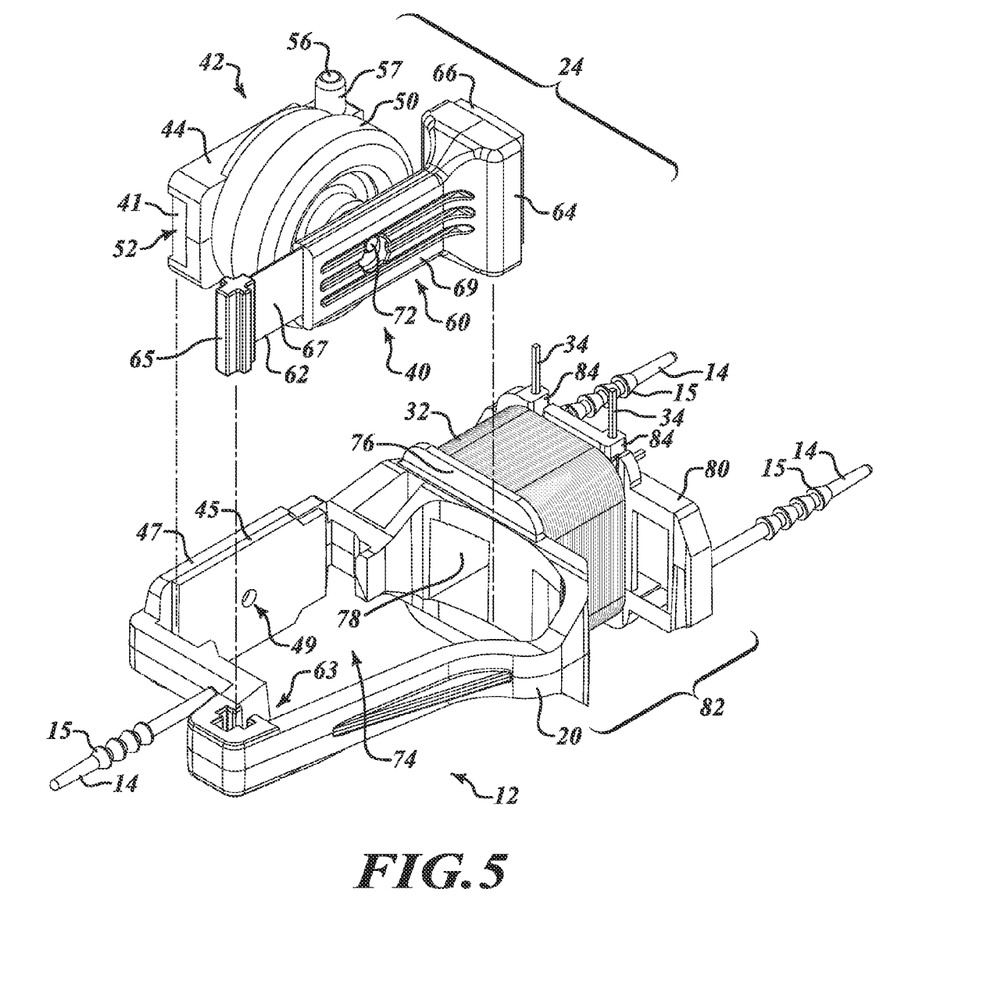

With reference to FIG. 5, after coupling the pump arm subassembly 40 to the manifold subassembly 42 to form the pump cartridge 24, the pump cartridge 24 may be coupled to the unitary frame body 20, such as, for example, by installing the pump cartridge 24 from one of opposing sides of the frame body 20 such that the anchoring device 65 at the proximal end 62 of the pump arm 60 engages the corresponding pump arm receiving aperture 63 provided in the frame body 20. Coupling the pump cartridge 24 to the frame body 20 may further include securing the pump cartridge 24 to the frame body 20 via the manifold 44 of the manifold subassembly 42 via a fastener 43 (e.g., a screw), as show in FIG. 6. For this purpose, each of the manifold seal 45 and the manifold backing portion 47 of the frame body 20 may be provided with an aperture 49 for receiving the fastener 43 therethrough for retaining the manifold 44 in engagement with the manifold seal 45 and frame body 20, as previously described. Coupling the pump cartridge 24 to the frame body 20 may further include inserting the pump cartridge 24 such that the retaining structures 51, 53 which are positioned to engage each of opposing ends of the manifold 44 of the pump cartridge 24 contact the manifold 44 and hold the manifold 44 into sealed engagement with the manifold seal 45. Coupling the pump cartridge 24 to the frame body 20 may further include fixedly attaching the pump cartridge 24 to the frame body 20 with the free end (i.e., the distal end 64) of the pump arm 60 supporting the permanent magnet 66 in close proximity to the lower platform or flange structure 76 of the frame body 20.

Figure 6:
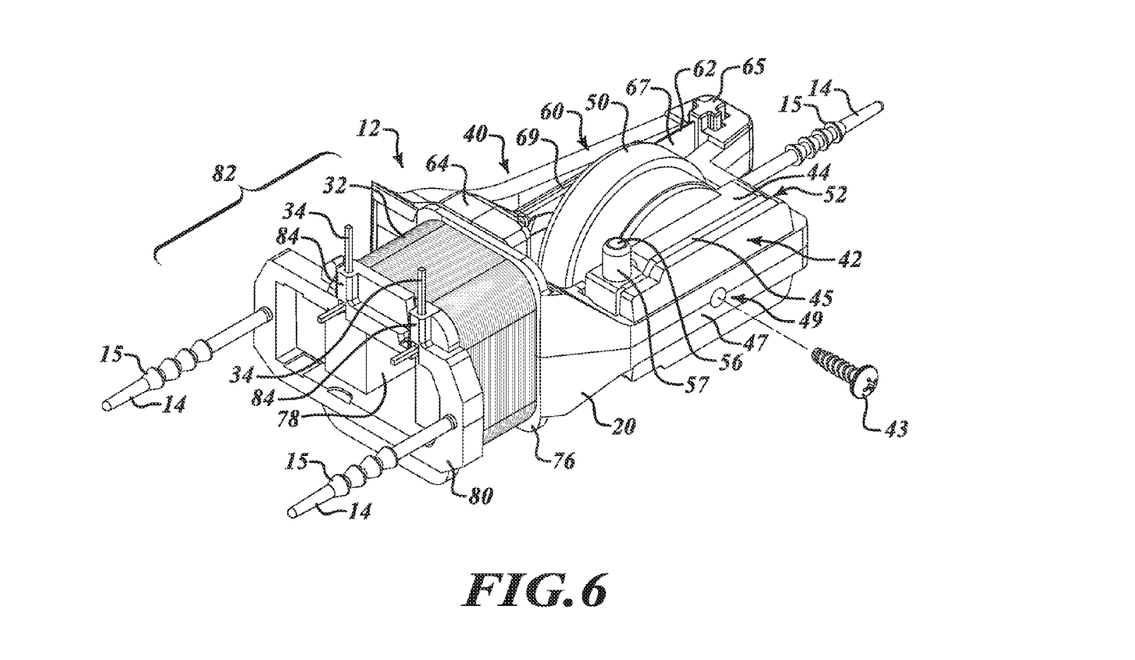

With reference to FIGS. 5 and 6, prior to or after coupling the pump cartridge 24 to the frame body 20, the method may include establishing the winding 32 about the bobbin or bobbin-like structure 82 of the frame body 20 and connecting the winding 32 to the electrical terminals 34 such that power may be supplied to the electromagnet arrangement 22 from an external AC power source during operation. According to the illustrated embodiment, the winding 32 is established around the hollow stem or core portion 78 of the frame body 20 between the lower platform or flange structure 76 and the upper flange or bulkhead 80, and the electrical terminals 34 may be insertably received in respective terminal structures 84 of the frame body 20.

Figure 7:
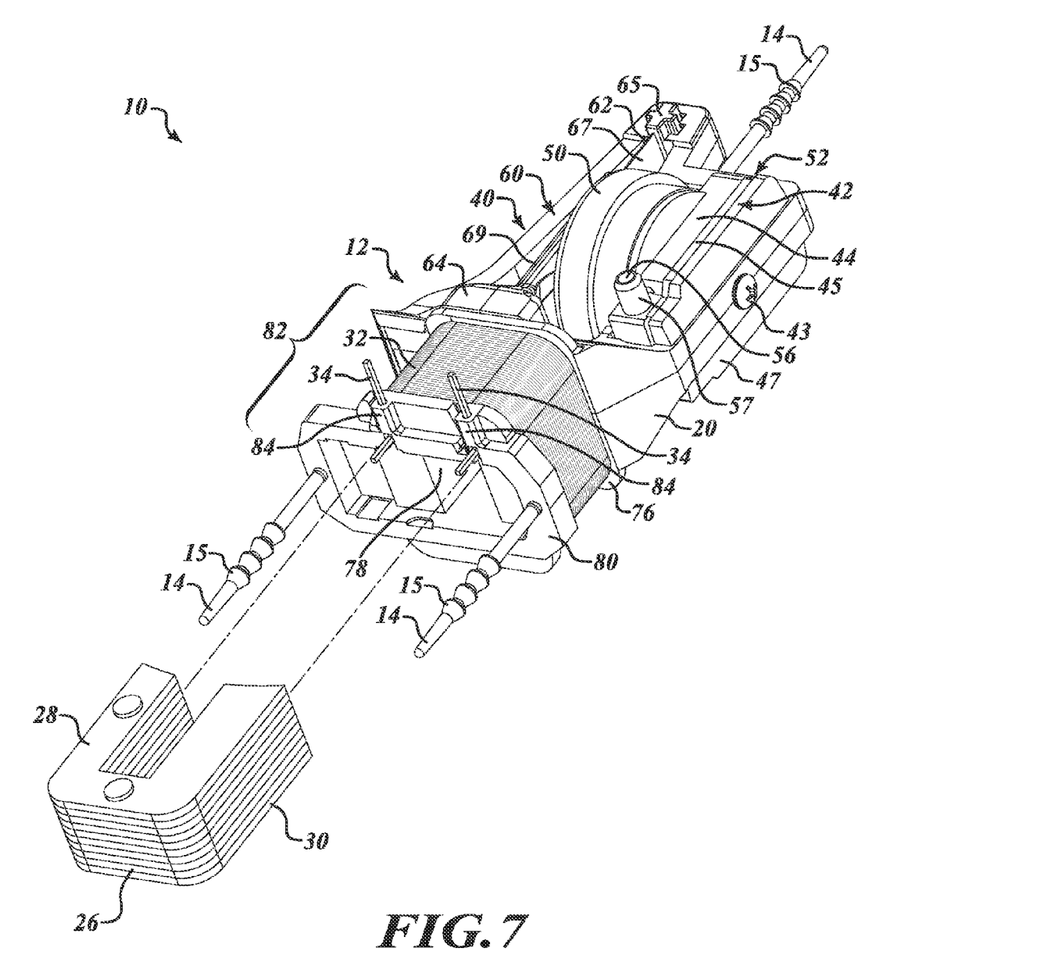

With reference to FIG. 7, after the pump cartridge 24 is fixedly secured to the frame body 20, the method may continue by inserting the electromagnet core 26 of the electromagnet arrangement 22 into the frame body 20 until ends of the opposing leg portions 28, 30 are in close proximity but slightly spaced away from the permanent magnet 66 supported at the free end (i.e., the distal end 64) of the pump arm 60. Inserting the electromagnet core 26 of the electromagnet arrangement 22 into the frame body 20 may include press-fitting or friction-fitting the electromagnet core 26 within corresponding apertures 77a, 77b, 79a, 79b provided in the lower platform or flange structure 76 and the upper flange or bulkhead 80. Inserting the electromagnet core 26 of the electromagnet arrangement 22 into the frame body 20 may further include passing one leg portion 30 of the electromagnet core 26 to pass through the winding 32 and the hollow stem or core portion 78 of the frame body 20, which is provided between the lower platform or flange structure 76 and the upper flange or bulkhead 80. Upon installation of the electromagnet core 26, the air supply device 10 may be substantially complete and ready for operation.

Figure 10:
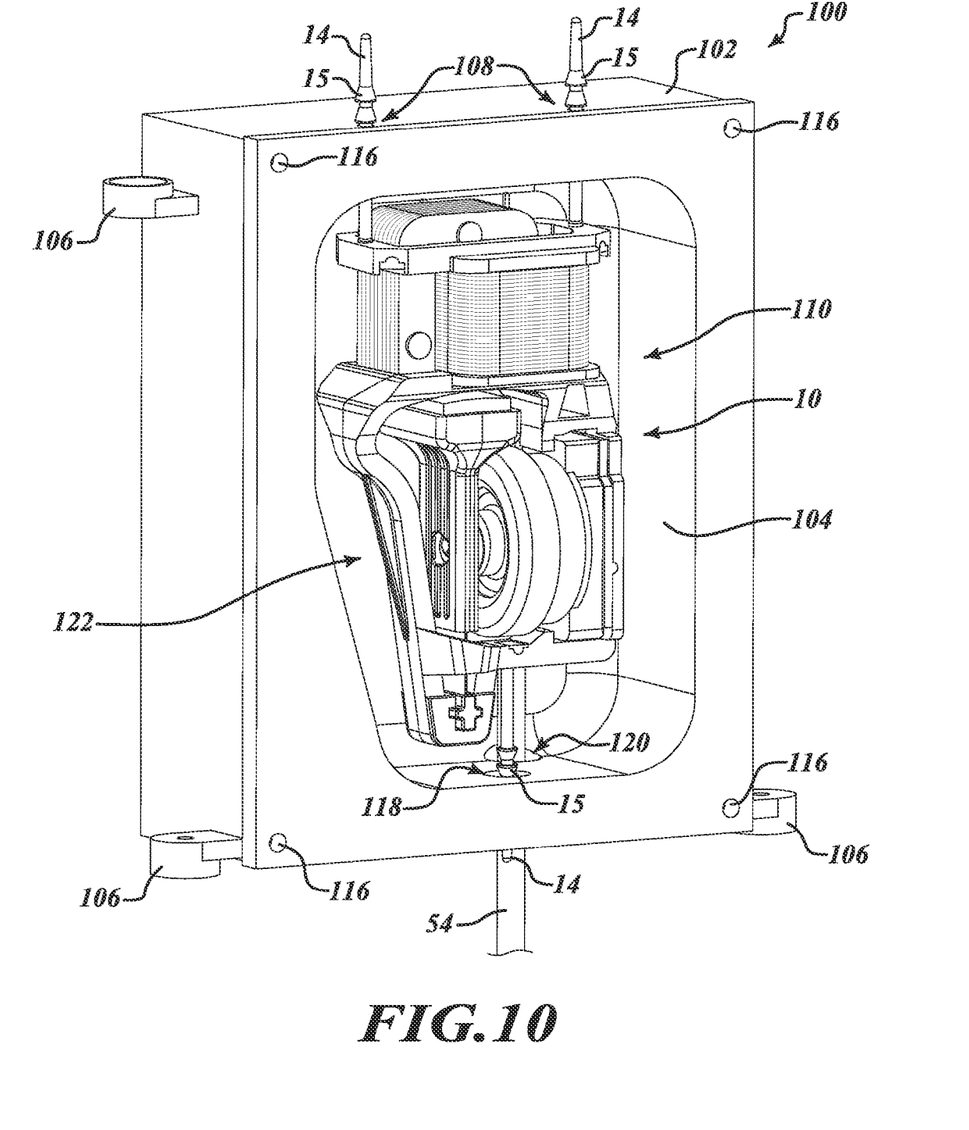
FIG. 10 is a perspective view of the air supply device of FIG. 1 shown suspended within a housing and surrounded by a sound deadening or muffling device, according to one example embodiment.

According to some embodiments, methods of manufacture may further include suspending the frame structure 12 within an internal housing cavity 110 via the tethers 14, as shown, for example, in FIG. 10. The method may further include providing a sound deadening or muffling device 104 or devices in the internal housing cavity 110 to reduce or minimize sound emanating from the housing 102. The method may further include coupling an outlet conduit 54 to the manifold 44, such as, for example, by attaching the outlet conduit 54 to an outlet nipple 57 of the manifold 44. An opposing end of the outlet conduit 54 may be connected directly or indirectly to a functional component of a host device, such as, for example, an air inlet port of a liquid diffusion device for air treatment purposes. The method may also include coupling the electromagnet arrangement 22 to an AC power source (e.g., 15V AC power source) and to a controller for controllably applying power to the electromagnet arrangement 22 during operation to generate an air stream as may be desired for a given application.

FIG. 10 shows an example pump assembly 100 wherein the air supply device 10 of FIG. 1 is suspended within an internal cavity 110 of a housing 102 and surrounded by a sound deadening or muffling device 104. The housing 102 provides a generally rigid enclosure and may include external mounts 106 for securing the housing 102 to a host device, such as, for example, an air treatment device having a diffusion head for diffusing a supply of liquid and discharging the diffused liquid into a surrounding environment for air treatment purposes. The housing 102 may further include a plurality of apertures 108 or other coupling features for receiving the tethers 14 of the example air supply device 10. The apertures 108 may be sized to receive the tethers 14 with the barbs 15 thereof compressed, such that, upon passing through the apertures 108, the barbs 15 may expand and retain the air supply device 10 within the internal cavity 110 of the housing 102. The housing 102 may further include one or more other apertures (not visible) for routing electrical wires or a cable to the air supply device from an AC power source and for routing the outlet conduit 54 to an exterior of the housing 102. The housing 102 may be provided in multiple pieces that are coupleable together to form a generally enclosed space. As an example, the housing 102 shown in FIG. 10 includes two opposing pieces that join together to enclose the air supply device 10, although one of the opposing pieces is not shown to reveal the internal cavity 110 and the air supply device 10 suspended therein. In some embodiments, the air supply device 10 may be oriented with the distal end 62 of the pivot arm 60 at a lower end of the housing 102 with the pump arm 60 standing generally upright.

With continued reference to FIG. 10, the sound deadening or muffling device 104 may be provided within the internal cavity 110 of the housing 102 to reduce sound emanating from the housing 102 during operation of the air supply device 10. For example, a foam structure may be provided within the internal cavity 110 to substantially surround and enclose the air supply device 10 apart from the tethers 14, outlet conduit 54 and electrical wires or cable (not shown) which may pass through the foam structure via one or more corresponding sized apertures 118, 120. The tethers 14, outlet conduit 54 and electrical wires or cable (not shown) may be particularly flexible to reduce or substantially eliminate the transmission of vibration from the air supply device 10 to the housing 102 or other surrounding structures. In some instances, the sound deadening or muffling device 104 may provide an air gap or space around the air supply device 10. A width of the air gap or space 122 may be generally constant or may vary around a perimeter of the air supply device 10. In some embodiments, the air gap or space may be greater than 3 mm but less than 8 mm. The sound deadening or muffling device 104 may also be provided in two or more pieces and may be coupled together or otherwise arranged together to substantially surround and enclose the air supply device 10 apart from the tethers 14, outlet conduit 54 and electrical wires or cable (not shown). The sound deadening or muffling device 104 may further include one or more coupling features, such as, for example, apertures 116, for attaching the sound deadening or muffling device 104 (or pieces thereof) to the housing 102.

Although embodiments of the air supply devices 10 described herein have been described in some instances as being suitable for use in connection with air treatment systems, particularly those including a diffusion head configured to diffuse liquid with the aid of an air stream moving there thorough, it will be appreciated that the air supply devices 10 may be used in a wide range of applications to provide an air stream for a variety of purposes.

Moreover, aspects, features and/or techniques of the various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ features, structures, functionality or concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. An air pump comprising:

a unitary pump frame having a closed perimeter structure which defines a pump assembly cavity and having a bobbin portion integrally formed therewith, the bobbin portion including a hollow core and opposing flanges;

an electromagnet arrangement including a winding wrapped directly around the hollow core of the bobbin portion of the unitary pump frame such that at least a portion of the winding is in contact with the unitary pump frame;

a diaphragm assembly coupled to and supported by the unitary pump frame within the pump assembly cavity, the diaphragm assembly including a movable diaphragm and a manifold;

a pump arm having a proximal end and a distal end, the proximal end of the pump arm coupled to the unitary pump frame to support the pump arm within the pump assembly cavity, and the distal end of the pump arm including a magnet to interact with the electromagnet arrangement to cause the pump arm to swing back and forth to displace the movable diaphragm during operation of the air pump; and a plurality of flexible, resilient tethers extending from the unitary pump frame for suspending the air pump within an internal cavity of a housing or a host device.

2. The air pump of claim 1 wherein the plurality of flexible, resilient tethers and unitary pump frame are formed via a multi-material injection molding process to form an integrated frame structure with tethers extending therefrom.

3. The air pump of claim 2 wherein the plurality of flexible, resilient tethers, the unitary pump frame and a manifold seal are formed via a multi-material injection molding process to form an integrated structure, and wherein the manifold of the diaphragm assembly is engaged with the manifold seal.

4. The air pump of claim 1 wherein the plurality of flexible, resilient tethers include barbs to selectively engage apertures of the housing or the host device to maintain the unitary pump frame suspended within the internal cavity.

5. The air pump of claim 1 wherein the unitary pump frame includes a pump arm receiving aperture sized and shaped to receive a corresponding portion of the proximal end on the pump arm in a press-fit or friction-fit.

6. The air pump of claim 1 wherein the unitary pump frame includes retaining structures positioned to engage each of opposing ends of the manifold of the diaphragm assembly to assist in coupling the manifold to the unitary pump frame.

7. The air pump of claim 6 wherein a manifold seal is provided adjacent a manifold receiving portion of the unitary pump frame and wherein the retaining structures assist in maintaining the manifold in sealed engagement with the manifold seal.

8. The air pump of claim 1 wherein the electromagnet arrangement includes an electromagnet core having a pair of legs, and wherein the unitary pump frame includes a bulkhead portion having a corresponding pair of apertures to receive the legs of the electromagnet core.

9. The air pump of claim 8 wherein the corresponding pair of apertures in the bulkhead portion of the unitary pump frame are sized and shaped to receive the legs of the electromagnet core in a press-fit or friction-fit.

10. The air pump of claim 1 wherein the unitary pump frame includes an upper bulkhead and terminals are provided at or proximate the upper bulkhead for supplying power to the electromagnet arrangement.

11. The air pump of claim 1 wherein the unitary pump frame is an open-sided structure that is configured to receive the diaphragm assembly and the pump arm as a pump cartridge in a direction transverse to a plane defined by an oscillating motion of the pump arm.

12. The air pump of claim 1 wherein the manifold includes a diaphragm chamber opposite a series of three distinct chambers including an air filter/muffler chamber, an air inlet chamber and an air outlet chamber.

13. The air pump of claim 1 wherein the manifold houses a plurality of one-way flapper valves including flapper members held in place via compressible valve retainer members.

14. The air pump of claim 1 wherein a constant air gap is defined between an upper surface of the magnet at the distal end of the pump arm and lower end surfaces of an electromagnet core of the electromagnet arrangement throughout a sweeping motion of the pump arm during operation.

15. An air treatment system comprising:
the housing
a diffusion head received in the housing; and
the air pump of claim 1 operably connected to the diffusion head for diffusing liquid contained in the housing.

16. The air treatment system of claim 15, further comprising:
a sound deadening or muffling device in the housing to reduce noise emanating therefrom.

17. The air treatment system of claim 16 wherein the sound deadening or muffling device substantially encloses the air pump and defines an air gap therebetween.

18. A manufacturing method comprising:
providing a unitary pump frame having a closed perimeter structure which defines a pump assembly cavity, and having a bobbin portion integrally formed therewith which includes a hollow core and opposing flanges;
wrapping a winding of an electromagnet arrangement directly around the hollow core of the bobbin portion of the unitary pump frame;
coupling a pump cartridge to the unitary pump frame within the pump assembly cavity defined by the closed perimeter structure of the unitary pump frame, the pump cartridge including a manifold subassembly and a pump arm subassembly;
thereafter coupling an electromagnet core of the electromagnet arrangement to the unitary pump frame such that at least a portion of the electromagnet core passes through the winding of the electromagnet arrangement; and
suspending the unitary pump frame within an internal housing cavity via a plurality of flexible, resilient tethers.

19. The method of claim 18, further comprising:
prior to coupling the pump cartridge to the unitary pump frame, press-fitting or friction-fitting the manifold subassembly into a movable diaphragm of the pump arm subassembly.

20. The method of claim 18 wherein coupling the pump cartridge to the unitary pump frame includes press-fitting or friction-fitting a proximal end of a pump arm of the pump arm subassembly into a corresponding aperture of the unitary pump frame.

21. The method of claim 20 wherein coupling the pump cartridge to the unitary pump frame further includes securing the manifold subassembly to the unitary pump frame with a fastener.

22. The method of claim 18 wherein coupling the electromagnet core of the electromagnet arrangement to the unitary pump frame includes press-fitting or friction-fitting leg portions of the electromagnet core into corresponding apertures of the unitary pump frame.

23. The method of claim 18, further comprising:
selectively adjusting a tension of one or more of the plurality of flexible, resilient tethers.

24. The method of claim 18, further comprising:
providing a sound deadening or muffling device in the internal housing to reduce noise emanating therefrom.

25. The method of claim 18, further comprising:
coupling an air outlet of the manifold subassembly to a liquid diffusion device.

* * * * *